(12) United States Patent
Pereira et al.

(10) Patent No.: US 12,178,457 B2
(45) Date of Patent: Dec. 31, 2024

(54) AUTOMATED METHOD OF REMOVING CLOG WITHIN LUMEN FOR DEBRIS REMOVAL

(71) Applicant: BOSTON SCIENTIFIC SCIMED, INC., Maple Grove, MN (US)

(72) Inventors: Peter J. Pereira, Mendon, MA (US); Martin Phelan, Sussex, NJ (US); Vincent Lai, Newtonwille, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 122 days.

(21) Appl. No.: 17/821,975

(22) Filed: Aug. 24, 2022

(65) Prior Publication Data

US 2022/0401119 A1 Dec. 22, 2022

Related U.S. Application Data

(63) Continuation of application No. 16/172,542, filed on Oct. 26, 2018, now Pat. No. 11,452,534.

(Continued)

(51) Int. Cl.
*A61B 17/22* (2006.01)
*A61B 17/32* (2006.01)
(Continued)

(52) U.S. Cl.
CPC ............... *A61B 17/22012* (2013.01); *A61B 17/320068* (2013.01); *B06B 1/16* (2013.01);
(Continued)

(58) Field of Classification Search
CPC ............ A61B 1/00087; A61B 1/00071; A61B 17/22012; A61B 17/22; A61B 17/22004;
(Continued)

(56) References Cited

U.S. PATENT DOCUMENTS

| | | |
|---|---|---|
| 4,735,604 A | 4/1988 | Watmough et al. |
| 5,582,617 A | 12/1996 | Klieman et al. |

(Continued)

FOREIGN PATENT DOCUMENTS

| | | |
|---|---|---|
| CN | 104619281 | 5/2015 |
| EP | 0198703 A2 | 10/1986 |

(Continued)

*Primary Examiner* — Katherine M Shi
(74) *Attorney, Agent, or Firm* — Bookoff McAndrews, PLLC

(57) ABSTRACT

A debris removal system includes an elongated shaft extending from a proximal end to a distal end and including a shaft lumen, the shaft being configured to be inserted through a bodily lumen to a target surgical site, a vibration motor coupled to the elongated shaft via a vibration collar, the vibration motor including a rotatable shaft and at least one weight coupled to the rotatable shaft, the weight being asymmetrically shaped about a central axis of the shaft such that rotation of the shaft creates vibrational energy along the length of the elongated shaft to dislodge debris within the target surgical site, and a vacuum pump connected to the elongated shaft and configured to vacuum dislodged debris from the target surgical site through the shaft lumen.

8 Claims, 3 Drawing Sheets

Related U.S. Application Data

(60) Provisional application No. 62/586,585, filed on Nov. 15, 2017.

(51) Int. Cl.
| | | |
|---|---|---|
| *B06B 1/16* | (2006.01) | |
| *A61B 17/00* | (2006.01) | |
| *A61B 18/00* | (2006.01) | |
| *A61B 18/26* | (2006.01) | |
| *A61B 90/00* | (2016.01) | |

(52) U.S. Cl.
CPC .............. *A61B 2017/00017* (2013.01); *A61B 2017/22079* (2013.01); *A61B 2017/32007* (2017.08); *A61B 2018/00511* (2013.01); *A61B 18/26* (2013.01); *A61B 2090/064* (2016.02); *A61B 2217/005* (2013.01); *A61B 2217/007* (2013.01); *A61B 2218/002* (2013.01); *B06B 2201/76* (2013.01)

(58) Field of Classification Search
CPC .... A61B 2217/005; A61B 2017/22079; A61B 2217/007; A61B 17/320068; A61B 17/2202; A61B 18/26; A61B 2017/00017; A61B 2017/32007; A61B 2018/00511; A61B 2090/064; A61B 2218/002; A61B 2017/00398; A61B 17/22031; A61B 17/32002
See application file for complete search history.

(56) References Cited

U.S. PATENT DOCUMENTS

| | | | |
|---|---|---|---|
| 6,083,170 A | 7/2000 | Ben-Haim | |
| 6,206,842 B1 | 3/2001 | Tu et al. | |
| 2004/0199049 A1 | 10/2004 | Parasher et al. | |
| 2005/0085826 A1 | 4/2005 | Nair et al. | |
| 2006/0264995 A1 | 11/2006 | Fanton et al. | |
| 2008/0051735 A1* | 2/2008 | Measamer | A61B 17/3417 606/185 |
| 2009/0082781 A1 | 3/2009 | Tran et al. | |
| 2011/0092892 A1* | 4/2011 | Nitsan | A61B 1/00068 604/524 |
| 2011/0105845 A1* | 5/2011 | Gordon | A61B 1/273 600/156 |
| 2012/0232780 A1 | 9/2012 | Delson et al. | |
| 2016/0022289 A1 | 1/2016 | Wan | |
| 2017/0238950 A1 | 8/2017 | Yang et al. | |
| 2018/0193052 A1* | 7/2018 | Govari | A61B 18/1485 |

FOREIGN PATENT DOCUMENTS

| | | | | |
|---|---|---|---|---|
| JP | 2010515469 | * | 5/2010 | ............ A61B 17/54 |
| JP | 2012223590 A | | 11/2012 | |
| KR | 20100081107 | | 7/2010 | |
| WO | WO-2007113808 A1 | * | 10/2007 | ......... A61B 17/1637 |
| WO | WO-2013051859 A2 | * | 4/2013 | ............ A61B 18/20 |

* cited by examiner

AUTOMATED METHOD OF REMOVING CLOG WITHIN LUMEN FOR DEBRIS REMOVAL

PRIORITY CLAIM

This present application is a Continuation of U.S. patent application Ser. No. 16/172,542 filed on Oct. 26, 2018; which claims priority to U.S. Provisional Patent Application Ser. No. 62/586,585 filed Nov. 15, 2017. The disclosures of the above application(s)/patent(s) are incorporated herewith by reference.

BACKGROUND

Many surgical procedures and other conditions require the removal of debris from the lumen or cavity of a patient. For example, urologists may need to remove a kidney stone. Typically, in such a case, the surgeon will perform laser lithotripsy to break up the kidney stone into multiple fragments and remove the stone fragments with a basket device. This process can be time consuming due to the fact that the surgeon can only remove one fragment at a time. In contrast, a vacuum system would allow a surgeon to remove more than a single fragment or stone at a time. However, a clogged lumen obstructs a vacuum system's path of suction, which reduces efficiency of removing stones with such a system and can be dangerous for the patient because it can cause a rise in the patient's cavity pressure. Thus, the present design provides a new method of removing or preventing a clog within a lumen full of debris during vacuum suctioning by using vibration energy.

SUMMARY

The present disclosure relates to a debris removal system. The system includes an elongated shaft extending from a proximal end to a distal end and including a shaft lumen, the shaft being configured to be inserted through a bodily lumen to a target surgical site, a vibration motor coupled to the elongated shaft via a vibration collar, the vibration motor including a rotatable shaft and at least one weight coupled to the rotatable shaft, the weight being asymmetrically shaped about a central axis of the shaft such that rotation of the shaft creates vibrational energy along the length of the elongated shaft to dislodge debris within the target surgical site, and a vacuum pump connected to the elongated shaft and configured to vacuum dislodged debris from the target surgical site through the shaft lumen.

In an embodiment, the vibration collar comprises a housing including a compartment, the compartment configured to house at least a portion of the vibration motor therein.

In an embodiment, a portion of the rotatable shaft extends one of proximally and distally from the compartment, the weight being coupled thereto.

In an embodiment, the weight is substantially shaped as a semi-circle.

In an embodiment, the vacuum pump is connected to the elongated shaft via tubing.

In an embodiment, the elongated shaft includes at least one sensor, the sensor transmitting sensor data relating to the target surgical site to the processor, wherein if the sensor detects an obstruction in the surgical site, the processor automatically turns the motor on.

The present disclosure also relates to a debris removal system. The system includes an sheath extending from a proximal end to a distal end and including an lumen extending therethrough, the sheath being configured to deliver fluid to a target surgical site, a scope device including an elongated shaft extending from a distal end thereof, the elongated shaft configured to be inserted through the lumen of the sheath, a vibration motor configured to be coupled to the elongated shaft, the vibration motor providing vibration energy along the length of the elongated shaft to dislodge debris within the target surgical site, and a vacuum pump connected to the elongated shaft to suction dislodged debris from the target surgical site through the elongated shaft.

In an embodiment, the system further comprises a processor, the processor being configured to automatically control the vibration motor.

In an embodiment, the elongated shaft includes at least one sensor, the sensor transmitting sensor data relating to the target surgical site to the processor, wherein if the sensor detects an obstruction in the surgical site, the processor automatically turns the motor on.

In an embodiment, the vibration motor is coupled to the elongated shaft via a vibration collar, the vibration collar extending from a proximal end to a distal end and including a housing configured to house the vibration motor.

In an embodiment, the vibration collar includes a channel extending from the proximal end to the distal end and sized and shaped to receive the elongated shaft therethrough.

In an embodiment, the vibration motor includes a rotatable shaft and at least one eccentric weight coupled thereto.

In an embodiment, the system further includes a collection canister, the collection canister being fluidly connected to both the scope device and the vacuum pump so that dislodged debris is drawn from the target surgical site to the collection canister.

In an embodiment, the sheath includes a seal configured to prevent back flow of fluid through the lumen.

In an embodiment, the scope device further comprises a handle, the handle including at least one button configured to manually control the vibration motor or the power of the vibration motor.

The present disclosure also relates to method of removing a clog within a lumen. The method includes inserting an elongated shaft into a target lumen, the elongated shaft extending from a proximal end to a distal end and including a channel extending therethrough, detecting, via at least one sensor coupled to the distal end of the elongated shaft, a blockage within the target lumen, dislodging the blockage from the target lumen via a vibration motor coupled to the elongated shaft, the vibration motor including a rotatable shaft and at least one weight coupled to the rotatable shaft, the weight being asymmetrically shaped about a central axis of the shaft such that rotation of the rotatable shaft creates vibrational energy along the length of the elongated shaft within the target lumen, and vacuuming the dislodged blockage from the target lumen and through the elongated shaft channel via a vacuum pump fluidly connected to the elongated shaft, wherein the at least one sensor automatically triggers the motor vibration motor to turn on when a blockage is detected.

In an embodiment, the method further comprises inserting an access sheath into the target lumen, the access sheath extending from a proximal end to a distal end and including an lumen extending therethrough, the access sheath being sized and shaped to receive the elongated shaft therein and configured to deliver fluid to a target lumen.

In an embodiment, the method further comprises drawing the dislodged blockage into a collection canister, the collection canister being fluidly connected to the scope device and the vacuum pump so that dislodged blockage is drawn from the target lumen to the collection canister.

In an embodiment, the method further comprises transmitting a sensor data relating to the target lumen to a processor.

In an embodiment, the method further comprises automatically signaling the vibration motor to turn off when the at least one sensor detects that conditions within the target lumen have normalized.

BRIEF DESCRIPTION

DETAILED DESCRIPTION

Figure 1:
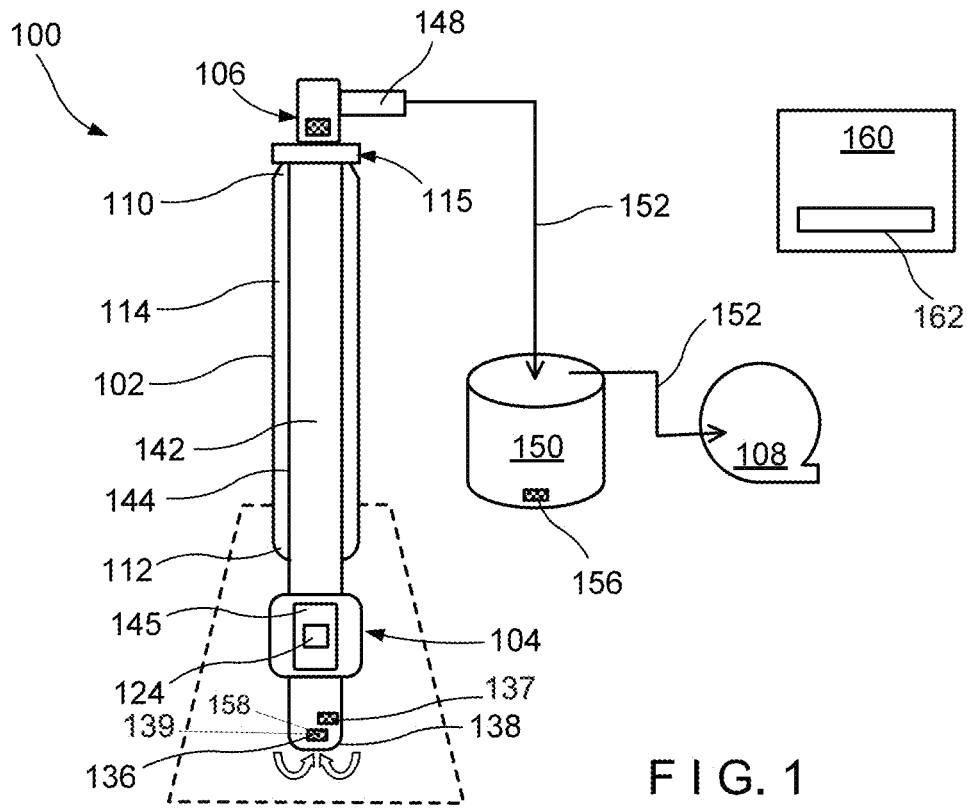
FIG. 1 shows a schematic illustration of a clog/debris removal system according to an exemplary embodiment of the present disclosure.

The present invention may be understood with respect to the following description and the appended drawings, wherein like elements are referred to with the same reference numerals. The present invention relates to devices, systems and methods for the removal of debris within a lumen through use of vibration energy. Exemplary embodiments describe a system including a lumen such as a catheter or scope an with sensors at the tip, a vibration motor and, in some embodiments, a LithoVue™ scope device. The system may include a vacuum source to suction the dislodged debris out of the lumen. Other exemplary embodiments describe a collection point for the debris. It should be noted that the terms "proximal" and "distal" as used herein are intended to refer to a direction toward (proximal) and away from (distal) a user of the device.

Figure 2:
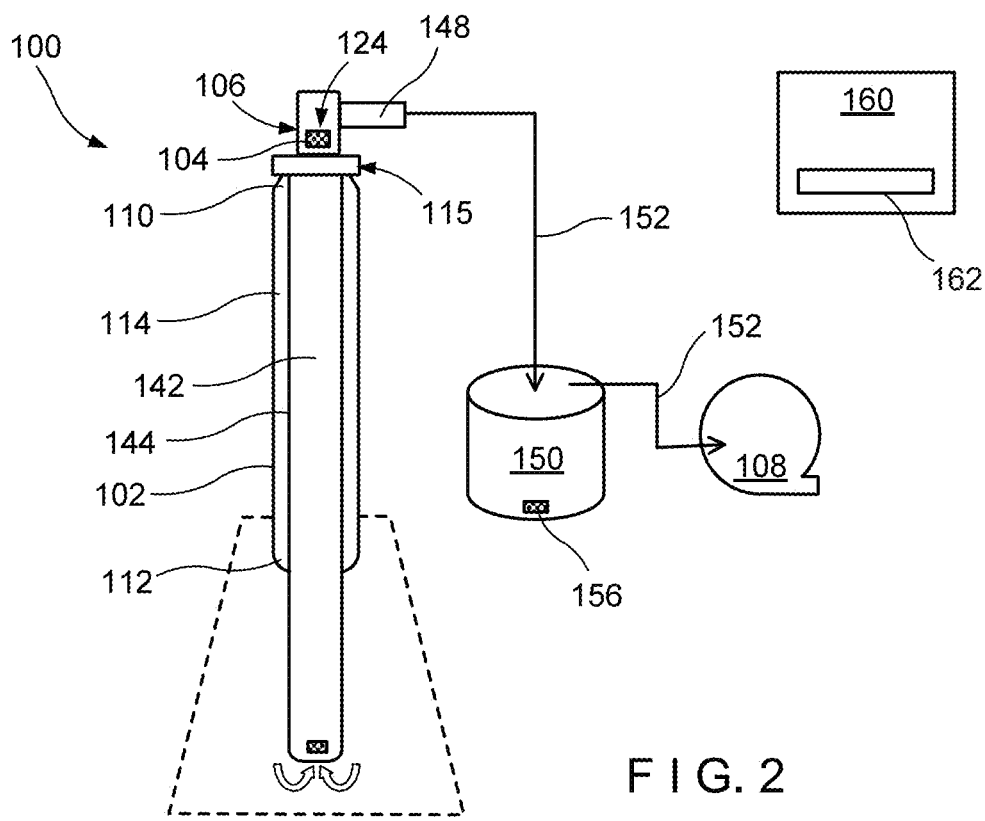
FIG. 2 shows a schematic illustration of the clog/debris removal system of FIG. 1 according to another exemplary embodiment of the present disclosure.

As shown in FIGS. 1-2, a system 100 according to an exemplary embodiment of the present disclosure comprises an access sheath 102 for providing access into a bodily lumen (e.g., along a tortuous path through a natural body lumen accessed via a naturally occurring body orifice), a shaft 144 and a vibration collar 104 with a vibration motor 124 for inducing energy within the lumen to dislodge debris therein. The system 100 may further comprise a scope assembly 106 including a handle 148, which remains outside of a living body while the shaft 144 is inserted through the sheath 102. The scope assembly 106 permits the user to control the vibration motor 124 via an actuator while the sheath 102 and shaft 144 are in the lumen. The scope assembly 106 also includes an actuator for a vacuum pump 108.

As shown in FIGS. 1-2, the access sheath 102 comprises an elongated member extending longitudinally from a proximal end 110 to a distal end 112 and including a lumen 114 extending therethrough. The sheath 102 may be substantially tubular and it may be made of any suitable biocompatible material such as polyurethane, plastic, or any other such material. Other suitable cross-sectional shapes such as elliptical, oval, polygonal, or irregular may also be contemplated. The sheath 102 may be flexible along its entire length or adapted for flexure along portions of its length. Alternatively, the sheath's distal end 112 may be flexible while a remaining proximal portion of the shaft 102 is rigid. Flexibility allows the sheath 102 to maneuver in circuitous lumens, while rigidity provides the required force to urge the sheath 102 forward. The sheath 102 provides a fluid path to deliver, for example, irrigation fluid to the target lumen or cavity. In an exemplary embodiment, the access sheath 102 includes a seal component 115 at the proximal end 110. The seal 115 may be integrally formed with the access sheath 102 or it may be a separate component that is coupled or clipped on to the access sheath 102. The seal 115 allows the shaft 144 of the scope 106 to be inserted through the access sheath 102 and into the target lumen without the system 100 losing pressure. Specifically, the seal 115 prevents back flow of the irrigation fluid provided through the access sheath lumen 114. It would be understood by one skilled in the art that the seal 115 does not need to be a tight seal but just allow enough pressure to be sustained within the access sheath 102 to push most of the irrigation fluid into the target lumen.

Figure 5:
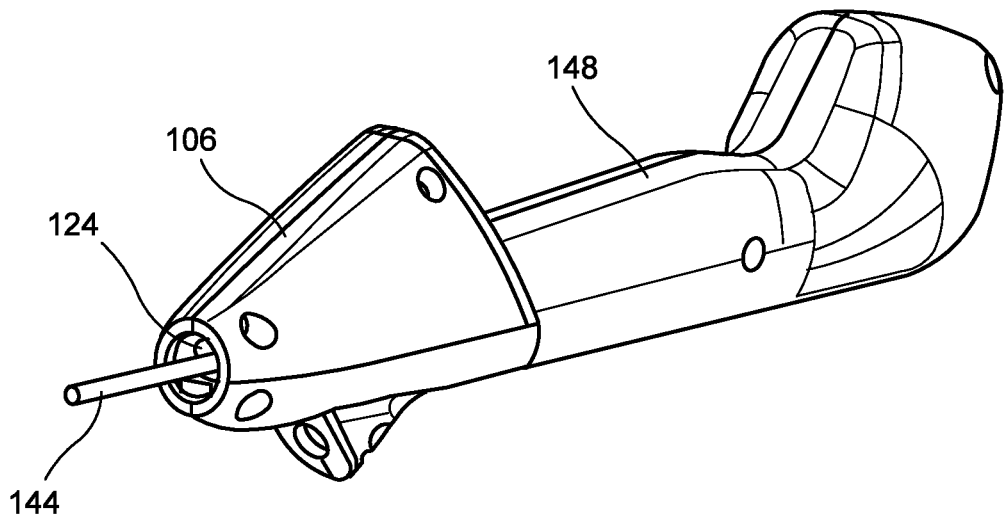
FIG. 5 shows a perspective view of a scope device with an internal vibration motor according to an exemplary embodiment.

In an exemplary embodiment depicted in FIGS. 1-2, a scope device 106 such as, for example, a ureteroscope, provides vacuum to the target lumen to remove debris therefrom. The scope 106 includes a scope shaft 144 sized and shaped to be inserted through the lumen 114 of the access sheath 102 and including a working channel 142. As shown in FIG. 1, the scope 106 may be connected to the vacuum pump 108 via a supply line (i.e., tubing 152), as described below. Thus, the vacuum pump 108 provides a source of vacuum pressure through the tubing and the working channel 142 of the shaft 144 to the target lumen within the patient. In an exemplary embodiment, the scope 106 may include at least one sensor 136 incorporated therein. For example, in one embodiment, the scope 106 may include a pressure transducer 137 at a distal tip 138 of the scope shaft 144 to measure pressure within, for example, the kidney. Alternatively, the pressure transducer 137 may be located on a guide wire, the access sheath 102 or externally along tubing 152. The scope 106 may include other sensors such as, in one embodiment, a camera 139, as described in further detail below. The scope 106 further includes a handle 148, as shown in FIG. 5. The handle 148 allows the user to control when the motor 124 is providing vibration energy to the shaft 144 via a motor on/off switch (not shown). In an exemplary embodiment, the manual motor buttons may override the system's automatic control of the motor 124. That is, if the system 100, through use of one of the sensors 136, has detected a blockage and signaled to the motor 124 to turn on, the user may override this command using the manual switches. In an embodiment, the handle 148 may also include a vacuum on/off button (not shown). Thus, the user has discretion to turn the vacuum on when debris, fluid, etc. is within the target lumen but can turn the vacuum off when suction is unnecessary.

Figure 3:
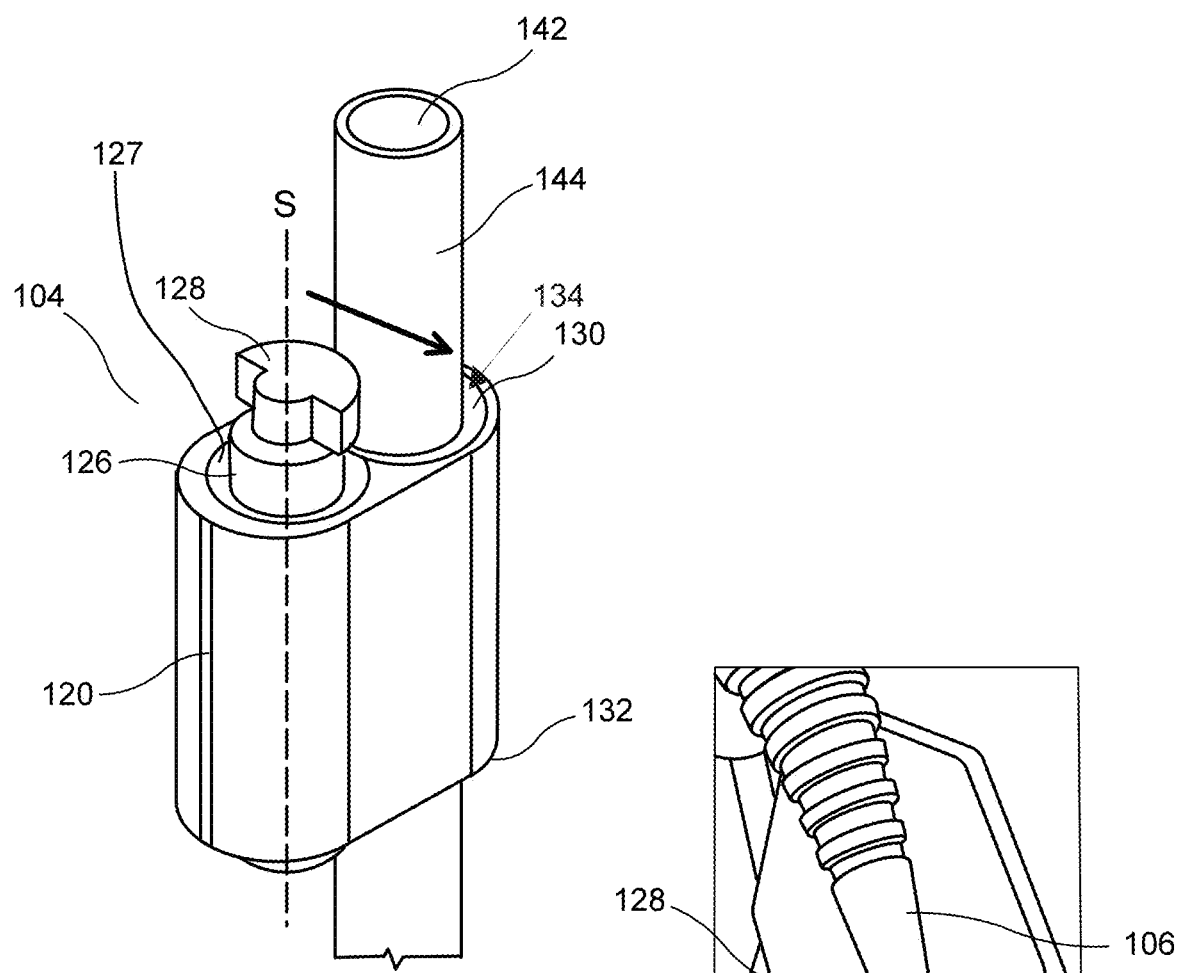
FIG. 3 shows a perspective view of a vibration collar of the clog/debris removal system according to an exemplary embodiment of the present disclosure.
Figure 4:
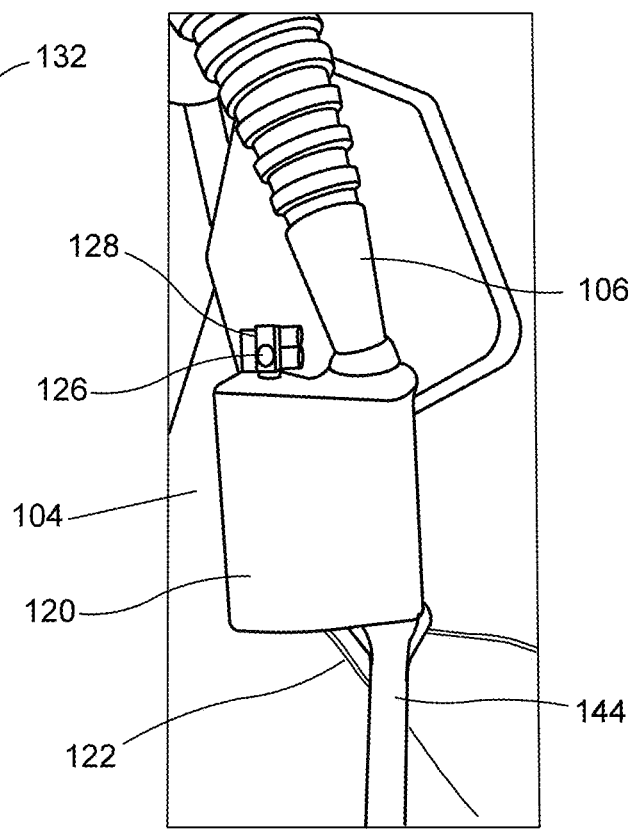
FIG. 4 shows a side view of the vibration collar of FIG. 3, according to an exemplary embodiment of the present disclosure.

The vibration collar 104 including the electric rotary vibration motor 124, as shown in FIGS. 3-4, is coupled to the scope shaft 144 to facilitate vibration along a length thereof. The vibration collar 104 extends from a proximal end 130 to a distal end 132 and includes a housing 120 comprising a compartment 127 for the vibration motor 124. The vibration motor 124, in this embodiment, has a rotatable shaft 126 extending along a central longitudinal axis, S, which may be fully disposed within the compartment 127 or, in another embodiment, may extend proximally or distally from the compartment 127, as shown in FIG. 3. The shaft 126 includes at least one eccentric weight 128 coupled thereto. For example, as shown in FIG. 3, the weight may be configured as a semi-circle. Because the weight 128 is asymmetrically shaped about the central axis S of the shaft 126, the shaft 126, when rotated, is off-balance about its axis toward the weighted side, causing a vibration when the shaft 126 rotates. Thus, the vibration frequency will be equal to the number of revolutions of the motor. As shown in the figure, the weight 128 may be coupled to a proximal end of the shaft 126 extending proximally from the housing 120. However, it will be understood that the weight 128 may be coupled to the shaft 126 at any point along its length, so long as the shaft 126 with the weight 128 attached is capable of rotating freely. Electric energy may be provided to the vibration motor 124 via wires 122 which provide a connection to an electrical source. In an example, the wires 122 are connected to the handle, which in turn has an electrical source such as, for example, a battery or an electrical line to an outlet. In an exemplary embodiment, the vibration motor 124 may automatically be activated by a sensor stimulus, as described in further detail below. In another exemplary embodiment, the motor 124 may also be manually activated by the user using the on/off switch on the handle 148.

Figure 6:
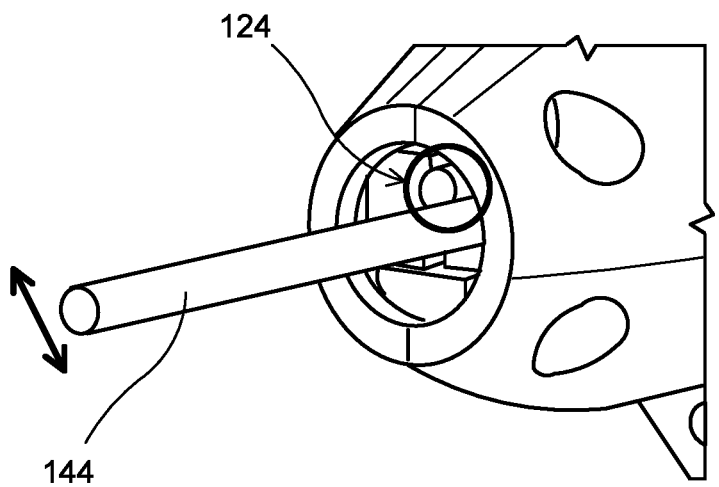
FIG. 6 shows a perspective view of the distal end of the scope with the vibration motor attached to the lumen according to the embodiment of FIG. 5.

The vibration collar 104 includes a channel 134 extending therethrough from the proximal end 130 to the distal end 132. The channel 134 is sized and shaped to receive the scope shaft 144 therethrough. For example, a diameter of the channel 134 may be equal to or slightly larger than the outer diameter of the shaft 144. The vibration collar 104 may be coupled to the shaft 144 via any coupling mechanism such as, for example, friction fit, a shrink tube, or by an adhesive. In an exemplary embodiment, shown in FIG. 6, the vibration collar 104 is coupled to the shaft 144 at a position within a distal end of the scope device 106. In an embodiment, the vibration collar 104 may be integrally formed with the scope 106 such that the vibrational energy passes along the entire length of the shaft 144 along the axis of the shaft 144. However, in another exemplary embodiment, shown in FIG. 2, the vibration collar 104 may be coupled to the shaft 144 at any user preferred point along its length. Thus, the vibrational energy may be focused on a specific length of the shaft 144 so that the vibrational energy may be more concentrated at the blockage point.

Although the access sheath 102, in the present embodiment, is used to provide a path for fluid to the target lumen and the scope shaft 144 is used to vacuum debris from the target lumen, one skilled in the art would understand that it is possible to reverse the flow path such that the scope shaft 144 provides fluid to the target lumen and the access sheath 102 is used to vacuum debris from the target lumen. However, in this embodiment where the flow path is reversed and the access sheath 102 is used to vacuum debris, the vibration collar 104 and vibration motor 124 is coupled to the access sheath 102. That is, the vibration energy is applied to the component—i.e., access sheath 102, scope shaft 144—that is connected to the vacuum pump 108 so that debris suctioned therethrough can be dislodged by the vibration motor 124. In another exemplary embodiment, the scope shaft 144 may include two lumens, one for suction and another for irrigation. In this embodiment, the vibration collar 104 and vibration motor 124 could be coupled to this shaft 144, eliminating the need for an access sheath. One ordinarily skilled in the art will understand that more than one vibration motor 124 could be coupled to the scope shaft 144.

In an exemplary embodiment, the scope 106 may be connected to a collection canister 150 as a collection point for the debris, tissue, fluid, etc. In an embodiment, tubing 152 may lead from the scope 106 to the collection canister 150, which is connected, via further tubing 152, to the vacuum pump 108, as shown in FIGS. 1-2. Thus, the vacuum pump 108 provides suction through the collection canister 150 and the scope working channel 142, creating low pressure in the collection canister 150 to draw the debris as well as fluid, etc. out of the target lumen and into the collection canister 150. In an exemplary embodiment, the collection canister 150 may include a weight sensor 156. The weight sensor (not shown) may be operatively connected to a processing device, as discussed in further detail below.

In an embodiment, the system 100 may include a processing device 160, such as a computer. The processing device 160 may be operatively connected to one or more system components such as, for example, the scope device 106, the vacuum pump 108 and/or the weight sensor 156. The processing device 160 is capable of performing various functions such as calculation, control, computation, etc. For example, the processing device 160 may receive signals or data from the sensors 136 of the system 100—i.e., pressure transducer, camera, flow meter—and determine from the data provided when and if the vibration motor 124 should be turned on. The processing device 160 may also be configured to include visual software/image recognition software that can detect visual noise from the camera. If the image provided to the processing device 160 is determined to not be sufficiently clear or sharp, the vibration motor 124 is turned on to break up the debris until the image is sharpened or cleared. The vibration motor 124 may be turned on for a temporary time (i.e., a predetermined period) or until the field of view is deemed to be sufficiently clear. In another example, if the pressure transducer at the distal tip of the scope 106 detects a rise in pressure within the cavity during suction of the debris, the system will assume that there is a blockage in the working channel 142 causing the pressure to rise and a signal will be sent to the processing device 160 which will automatically turn the vibration motor 124 on. An exemplary rise in pressure may be approximately 5-10% from the baseline pressure. In another exemplary embodiment, the system 100 may include a flow meter 158. In this embodiment, if the flow meter detects a reduction in fluid flow within the working channel 142, a signal will be sent to the processing device 160 which will turn on the vibration motor 124 until the clog is dislodged and the fluid flow returns to a normal flow rate. In yet another exemplary embodiment, if the collection canister 150 includes a weight sensor 156, the collection canister 150 is weighed during the procedure. If the sensor 156 detects no change in weight for a predetermined amount of time such as, for example, 5-10 seconds, the system will assume that there is a blockage in the working channel 142 and a signal may be sent to the processing device 160 to automatically turn on the vibration motor 124.

In an exemplary embodiment, the processing device 160 includes a user interface component such as a touch screen interface 162. The user interface may include a display screen as well as touch buttons. The user interface allows the user to turn on/off various functions of the system 100 such as, for example, the vibration motor 124. That is, in an embodiment, the user is able to manually control the vibration motor 124 from the user interface or from the scope handle 148. In another embodiment, the user interface may include vibration motor control button in lieu of the scope handle 148. Each of the various sensors 136 being used may be managed by the user interface, which also allows the user to add, change, or discontinue use of the various sensors. The user interface component may also be used to change the vibration motor 124 between automatic and manual modes for various procedures.

An exemplary method for removing debris from a clogged working channel 142 includes inserting the distal end of the access sheath 102 into a target channel and advancing the sheath 102 therethrough to a target cavity within, for example, the kidney. In some embodiments, irrigation fluid may be provided through the lumen 114 of the access sheath 102 and into the target channel. Once the access sheath 102 is positioned within the kidney as desired, the shaft 144 of the scope 106 is advanced through the lumen 114 of the sheath 102 until the distal end thereof extends past the distal end 112 of the access sheath 102. As the scope 106 is advanced into the target lumen, sensors 136 positioned on the distal end of the scope shaft 144 provide feedback to the processing device 160 regarding conditions of the target anatomy in which the scope 106 is positioned as well as conditions within the working channel 142 of the scope shaft 140, which may then be displayed on a display screen. During, for example, a lithotripsy, a kidney stone is broken up into multiple fragments and the scope 106 is used to suction the fragments through the working channel 142 of the shaft 144. While the debris is being suctioned through the system 100, if the sensors 136 determine that there is a blockage clog formed by, for example, a kidney stone fragments, in the working channel 142, the sensors 136 will automatically trigger the motor 124 to turn on. Because the motor 124 and motor collar 104 are coupled to the scope shaft 144, vibration energy is provided along the length of the shaft 144 to dislodge the debris and break up the clog within the working channel 142. Once the debris is dislodged, the vacuum pump 108 continues to vacuum the debris from the working channel 142 of the shaft 144 of the scope 106 and into the collection canister 150. As the sensors 136 detect that conditions have normalized (i.e., the obstruction has been removed), the system 100 will turn off the motor 124. At any point in the procedure, the user may switch the system 100, via the user interface 162 or other physical switch, so that components thereof, such as the motor 124, vacuum pump 108, etc., may be adjusted manually. Manual adjustment may occur through use of the buttons on the scope handle or through buttons on the user interface.

It will be appreciated by those skilled in the art that the current devices and methods are not limited to the disclosed embodiments. For example, the disclosed debris removal system 100 may be used in various other procedures such as, for example, hysteroscopies, cystoscopies, etc. Thus, the system 100 is not limited to use with a ureteroscope but may be used with other devices such as cystoscopes, hysteroscopes or any other device with a shaft inserted into a body channel/lumen/cavity.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiments disclosed, but rather modifications are also covered within the scope of the present invention as defined by the appended claims.

What is claimed is:

1. A system for removing debris during a medical procedure, comprising:
   a sheath extending from a sheath proximal end to a sheath distal end and including a lumen extending therethrough, the sheath being configured to deliver fluid to a target surgical site;
   a scope device including an elongated shaft extending from a scope device distal end, the elongated shaft having a working channel extending therethrough and being configured to be inserted through the lumen of the sheath;
   a vibration motor coupled to the elongated shaft and configured to transmit vibration energy along a length of the elongated shaft to dislodge debris within the target surgical site, wherein the vibration motor is coupled to the elongated shaft via a vibration collar, the vibration collar extending from a vibration collar proximal end to a vibration collar distal end and including a housing configured to house the vibration motor;
   a vacuum pump connected to the elongated shaft to suction dislodged debris from the target surgical site through the elongated shaft; and
   a processor configured to receive fluid flow data from a flow meter at a distal end of the elongated shaft, the flow meter configured to measure a fluid flow rate in the working channel.

2. The system of claim 1, wherein the processor is configured to automatically turn the vibration motor on when the flow meter detects that the fluid flow rate is less than a desired fluid flow rate.

3. The system of claim 1, wherein the elongated shaft includes at least one sensor, the at least one sensor transmitting sensor data relating to the target surgical site to the processor and wherein if the at least one sensor detects an obstruction in the target surgical site, the processor automatically turns the vibration motor on.

4. The system of claim 1, wherein the vibration collar includes a channel extending from the vibration collar proximal end to the vibration collar distal end and sized and shaped to receive the elongated shaft therethrough.

5. The system of claim 1, wherein the vibration motor includes a rotatable shaft and at least one eccentric weight coupled thereto.

6. The system of claim 1, further comprising a collection canister, the collection canister being fluidly connected to both the scope device and the vacuum pump so that dislodged debris is drawn from the target surgical site to the collection canister.

7. The system of claim 1, wherein the sheath includes a seal configured to prevent back flow of fluid through the lumen.

8. The system of claim 1, wherein the scope device further comprises a handle, the handle including at least one button configured to manually control the vibration motor or a power of the vibration motor.

* * * * *